(12) United States Patent
Leikauf (10) Patent No.: US 9,492,408 B2
(45) Date of Patent: Nov. 15, 2016

(54) PROTECTION FROM CHEMICAL-INDUCED ACUTE LUNG INJURY

(71) Applicant: University of Pittsburgh—Of the Commonwealth System of Higher Education, Pittsburgh, PA (US)

(72) Inventor: George Douglas Leikauf, Gibsonia, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1 day.

(21) Appl. No.: 14/522,522

(22) Filed: Oct. 23, 2014

(65) Prior Publication Data

US 2015/0119468 A1 Apr. 30, 2015

Related U.S. Application Data

(60) Provisional application No. 61/895,323, filed on Oct. 24, 2013.

(51) Int. Cl.
| | | |
|---|---|---|
| C07C 15/30 | (2006.01) |
| A61K 31/164 | (2006.01) |
| A61B 10/02 | (2006.01) |
| A61K 45/06 | (2006.01) |
| A61B 5/087 | (2006.01) |
| A61B 5/145 | (2006.01) |
| A61B 5/055 | (2006.01) |
| A61B 5/00 | (2006.01) |
| A61B 5/08 | (2006.01) |

(52) U.S. Cl.
CPC ............. *A61K 31/164* (2013.01); *A61B 10/02* (2013.01); *A61K 45/06* (2013.01); *A61B 5/055* (2013.01); *A61B 5/08* (2013.01); *A61B 5/087* (2013.01); *A61B 5/0871* (2013.01); *A61B 5/14542* (2013.01); *A61B 5/4848* (2013.01)

(58) Field of Classification Search
None
See application file for complete search history.

(56) References Cited

FOREIGN PATENT DOCUMENTS

WO WO 2005/097119 10/2005

OTHER PUBLICATIONS

Fanucchi et al (Am J Respir Cell Mol Biol, 2012; 46(5):599-606, published originally in press Dec. 8, 2011).*
Lai et al., "Inhibition of the phosphatase PTEN protects mice against oleic acid-induced acute lung injury," *British Journal of Pharmacology* 156, 189-200 (2009).

(Continued)

*Primary Examiner* — Marcos Sznaidman
*Assistant Examiner* — Rayna B Rodriguez
(74) *Attorney, Agent, or Firm* — Klarquist Sparkman, LLP (57) ABSTRACT

Methods are provided herein for treating an individual having a disease, disorder or condition affecting the lungs, wherein said disease, disorder, or condition of the lung is an acute lung injury. In specific embodiments, the acute lung injury is chemical induced acute lung injury (CIALI). In some embodiments, the methods are provided for treating or protecting a subject from chemical induced acute lung injury that include administering to the subject a therapeutically effective amount of a phosphatase located on chromosome 10 (PTEN) inhibitor such as N(9,10-dioxo-9,10-di-hydro-phenanthren-2-yl)pivalamide (SF1670). In some embodiments, the method products a subject from CAILI or reduces CAILI that results from a subsequent exposure to a chemical that induces chemical induced acute lung injury.

**15 Claims, 4 Drawing Sheets
(1 of 4 Drawing Sheet(s) Filed in Color)**

(56) References Cited

OTHER PUBLICATIONS

Leikauf et al., "Integrative assessment of chlorine-induced acute lung injury in mice" *Am. J Respir. Cell Mol. Biol.* 47(2):234-244 (Aug. 2012).

Li et al., "Pretreatment with phosphatase and tensin homolog deleted on chromosome 10 (PTEN) inhibitor SF1670 augments the efficacy of granulocyte transfusion in a clinically relevant mouse model," *Blood* 117(24):6702-6713 (Jun. 16, 2011).

Mihai et al., "PTEN inhibition improves wound healing in lung epithelia through changes in cellular mechanics that enhance migration," *Am. J Physiol. Lung Cell Mol. Physiol.* 302: L287-L299 (2012)(First published Oct. 28, 2011).

* cited by examiner

PROTECTION FROM CHEMICAL-INDUCED ACUTE LUNG INJURY

PRIORITY CLAIM

This claims the benefit of U.S. Provisional Application No. 61/895,323, filed Oct. 24, 2013, which is incorporated by reference herein in its entirety.

ACKNOWLEDGMENT OF GOVERNMENT SUPPORT

This invention was made with government support under Grant No. U01ES15675 awarded by the National Institutes of Health. The government has certain rights in the invention.

FIELD

This relates to the treatment of pulmonology, specifically to methods for treating an acute lung injury such as chemical-induced acute lung injury (CALI) using a phosphatase located on chromosome 10 (PTEN) inhibitor.

BACKGROUND

Even without signs of external injury, chemical exposure can produce severe trauma to internal target organs including the lungs, heart, gastrointestinal tract, eyes, and the central nervous system. Of these injuries, the extent of lung injury often is the most critical to survival. Chemical-Induced Acute Lung Injury (CIALI) can be viewed as a molecular cascade mounting over hours and days subsequent to even a transient incident. Unfortunately, CIALI is a likely consequence of terrorist attacks of multiple possible scenarios including intentional detonation of chemical plants, railroad car derailment, or chemical truck hijacking and can result in exposure of short (1-2 h) or long duration (days). Chemicals of high concern include chlorine, phosgene, sulfuric acid, ammonia, and acrolein. A need remains for agents that can be used to prevent and treat CIALI.

SUMMARY

Methods are provided herein for treating an individual having a disease, disorder or condition affecting the lungs, wherein said disease, disorder, or condition of the lung is an acute lung injury. In some embodiments, the acute lung injury is CIALI.

In some embodiments, the methods are provided for treating or protecting a subject from CIALI that include administering to the subject a therapeutically effective amount of a phosphatase located on chromosome 10 (PTEN) inhibitor. In specific non-limiting examples, the PTEN inhibitor includes N(9,10-dioxo-9,10-di-hydrophenanthren-2-yl)pivalamide (SF1670).

In additional embodiments, the PTEN inhibitor can be used to protect a subject from the CIALI. In yet other embodiments, the chemical that induces the acute lung injury is chlorine, phosgene, sulfuric acid, ammonia, or acrolein. In further embodiments, the subject can be human.

In further embodiments, the method protects a subject from CAILI or reduces CAILI that results from a subsequent exposure to a chemical that induces chemical induced acute lung injury.

The foregoing and other objects, features, and advantages of the invention will become more apparent from the following detailed description, which proceeds with reference to the accompanying figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Methods are provided herein for treating an individual having a disease, disorder or condition affecting the lungs, wherein said disease, disorder, or condition of the lung is an acute lung injury. In specific embodiments, said acute lung injury is one or more of physical trauma, injury due to drug or chemotherapeutic toxicity (e.g., toxicity due to treatment with bleomycin, cyclophosphamide, nitrofurantoin, methotrexate, combination 5-fluorouracil and oxaliplatinum therapy or the like), a radiation-induced injury, a chemical injury, e.g., a chemical burn, smoke inhalation, exposure to a toxic substance, or chemically-induced pneumonia.

In some embodiments, methods are provided for treating or protecting a subject from chemical induced acute lung injury, comprising administering to the subject a therapeutically effective amount of a PTEN inhibitor, such as, but not limited to, N(9,10-dioxo-9,10-dihydrophenanthren-2-yl) pivalamide (SF1670). In some embodiments, the chemical that induces the CAILI is chlorine, phosgene, sulfuric acid, ammonia, and/or acrolein. The subject can be human. The subject can be military personnel. The subject can be healthy. In some embodiments, protecting the subject comprises preventing chemical induced acute lung injury or reducing chemical induced acute lung injury form a subsequent exposure to the chemical insult, such as exposure to one or more of chlorine, phosgene, sulfuric acid, ammonia, and acrolein.

In additional embodiments, the PTEN inhibitor, such as N(9,10-dioxo-9,10-di-hydrophenanthren-2-yl)pivalamide (SF1670), can be administered before or after exposure to the chemical agent. In some embodiments the SF1670 is administered about 5 to about 60 minutes after exposure to a chemical that induces chemical induced acute lung injury, such as about 10 to about 50 minutes after exposure to the chemical, about 20 to about 40 minutes after exposure to the chemical, or about 25 to about 35 minutes after exposure to the chemical. For example, the N(9,10-dioxo-9,10-di-hydrophenanthren-2-yl)pivalamide (SF1670) is administered about 30 minutes after exposure to the chemical.

In additional embodiments, the methods can include detecting an improvement in one or more symptoms of lung injury by one or more of spirometry, peak flow meter, detection of $CO_2$ levels in the blood, radiography, CT scanning, magnetic resonance imaging, bronchoscopy, or broncheolar lavage.

TERMS

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, for example, "comprising an antibody" means "including an antibody" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided.

Acute lung injury (ALI): An acute pulmonary disorder that can be induced directly by inhalation of toxic chemicals (chemical induced acute lung injury) or other means or can be induced indirectly by systemic injury. ALI is characterized by a rapid onset (for example, over a few hours to few days, such as three days or less or one day or less) of one or more of dyspnea, hypoxemia, and diffuse infiltrates on chest x-ray in the absence of elevated left atrial pressure.

Acute lung injury includes subcategories of respiratory distress syndromes including infant respiratory distress syndrome (IRDS), hyaline membrane disease (HMD), neonatal respiratory distress syndrome (NRDS), respiratory distress syndrome of newborn (RDSN), surfactant deficiency disorder (SDD), adult respiratory distress syndrome (ARDS) acute respiratory distress syndrome (ARDS), respiratory complication from systemic inflammatory response syndrome (SIRS), or severe acute respiratory syndrome (SARS). Acute lung injury can be induced by exposure to toxic chemicals such as chlorine, phosgene, sulfuric acid, ammonia, or acrolein. Acute lung injury can also be caused by exposure to radition.

The degree of hypoxemia in ALI may be moderate as defined as a ratio of arterial oxygen partial pressure over inspiratory oxygen fraction $(PaO_2/FiO_2)<300$ (which is sometimes referred to as ALI or moderate ARDS) or severe as a $PaO_2/FiO_2<200$ (which is sometimes referred to as ARDS when distinguished from ALI or moderate ARDS) (see PCT Publication No. 2010/028845 A2). Diagnosis is usually made by clinical presentation, ABGs (arterial blood gas analyses) and imaging studies.

Standard treatment methods for acute lung injury include lung-protective, low tidal volume mechanical ventilation and supportive therapy. Acute hypoxemia respiratory failure is due to pulmonary edema (reviewed in Honing, E. G., and Ingram, R. H., Jr., in: *Harrison's Principles of Internal Medicine*, 14th Edition, A. S. Fauci, et al. (eds.), McGraw-Hill, N.Y., pp. 1483-1486, 1998; and Goodman, R. B., et al., *Am J. Respir. Crit. Care Med.* 154:602-11, 1996). ALI develops rapidly after a predisposing condition triggers a systemic inflammatory response, and is most strongly associated with conditions that produce direct alveolar injury or direct injury via the pulmonary capillary bed, such as aspiration, diffuse infection, toxic inhalation, direct injury to the alveolar epithelium, or sepsis syndrome. For example, after a toxic inhalation respiratory distress can develop, for example, substantially immediately or within a few hours, such as one to three hours, within one hour, or within two hours, of toxic exposure.

ALI can be the consequence of unregulated over-expression of usual systemic inflammatory responses to infection and/or injury. ALI can also occur in the absence of leukocyte mediated events and therefore is not always associated with inflammation. Injury involves the alveolar epithelium and the pulmonary capillary endothelium, and results in a complex cascade of events. Injury is produced by cellular events associated that can include loss of epithielial and endothelial barrier function aggravated by activation of neutrophils, macrophages, monocytes, and lymphocytes producing various cytokines, in turn producing cellular activation, chemotaxis, and adhesion.

Animal: Living multi-cellular vertebrate organisms, a category that includes, for example, mammals and birds. The term mammal includes both human and non-human mammals. Similarly, the term "subject" includes both human and veterinary subjects. Therefore, the general term "subject" is understood to include all animals, including, but not limited to, humans, or veterinary subjects, such as other primates, dogs, cats, horses, and cows.

Anti-Inflammatory Agent: Any of various medications that decrease the signs and symptoms (for example, pain, swelling, or shortness of breath) of inflammation. Corticosteroids are exemplary potent anti-inflammatory medications. Non-steroidal anti-inflammatory agents are also effective exemplary anti-inflammatory agents and do not have the side effects that can be associated with steroid medications.

Antioxidant: A molecule that inhibits the oxidation of other molecules. Generally, antioxidants remover free radical intermediates and can inhibit oxidation reactions. Antioxidants are classified into two broad divisions, depending on whether they are soluble in water (hydrophilic) or in lipids (lipophilic). In general, water-soluble antioxidants react with oxidants in the cell cytosol and the blood plasma, while lipid-soluble antioxidants protect cell membranes from lipid peroxidation. Antioxidants include ascorbic acid, glutthione, lipoic acid, uric acid, carotenes, vitamin E, and ubiquinol. Antioxidant liposomes (see Hoesel et al., Antioxid. Redox. Signal 10: 973-81, 2008, incorporated herein by reference) can be used to protect subjects from CALI.

Bronchodilator: An antispasmodic or other agent that dilates a bronchus or bronchiole. Bronchodilators relax the smooth muscles of the airways, allowing the airway to dilate. Bronchodilator medicines do not counteract inflammation.

Expectorant: A drug or chemical substance that induces the ejection of mucus, phlegm, and other fluids from the lungs and air passages, for example by coughing.

Expiratory Flow Rate: The rate at which air is expelled from the lungs during exhalation. A subject's maximum expiratory flow is measured by a simple pulmonary test; in performing the test, a subject first takes as deep a breath as possible, then exhales as rapidly and as completely as possible into a machine known as a spirometer, which measures the rate of exhalation. Forced expiratory flow 25-75 (FEF 25-75) is a measurement of the forced expiratory flow determined over the midportion of a forced exhalation. An increase in the forced expiratory flow (FEF) or FEF 25-75 reflects a decrease in bronchoconstriction and an improvement in pulmonary function.

Forced Expiratory Volume (FEV): The forced expiratory volume is the volume of air resulting from the forced expiratory flow test in which a subject first inspires maximally to the total lung capacity, then exhales as rapidly and as completely as possible. The forced expired volume in one second (FEV1) represents the maximum expiratory air volume a subject can produce during a one-second interval. An increase in FEV or FEV1 reflects a decrease in bronchoconstriction and an improvement in pulmonary function.

Forced Vital Capacity (FVC): The volume of air resulting from the forced expiratory flow test in which a subject first inspires maximally to the total lung capacity, then exhales as rapidly and as completely as possible. An increase in FVC reflects a decrease in bronchoconstriction and an improvement in pulmonary function.

Immune response: A response of a cell of the immune system, such as a B cell or T cell to a stimulus. In one embodiment, the response is an inflammatory response.

Inflammatory response: An accumulation of white blood cells, either systemically or locally at the site of inflammation. The inflammatory response may be measured by many methods well known in the art, such as the number of white blood cells (WBC), the number of polymorphonuclear neutophils (PMN), a measure of the degree of PMN activation, such as luminal enhanced-chemiluminescence, or a measure of the amount of cytokines present.

Inspiratory Flow Rate: The rate at which air travels into the lungs during inspiration. Inspiratory flow is measured by a simple pulmonary test; in performing the test the subject takes as deep and rapid a breath as possible from a machine known as a spirometer, which measures the rate of inspiration. An increase in inspiratory flow rate reflects a decrease in bronchoconstriction and an improvement in pulmonary function.

Isolated: An "isolated" biological component (such as a nucleic acid, peptide or protein) has been substantially separated, produced apart from, or purified away from other biological components in the cell of the organism in which the component naturally occurs, i.e., other chromosomal and extrachromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell as well as chemically synthesized nucleic acids.

Leukocyte: Cells in the blood, also termed "white cells," that are involved in defending the body against infective organisms and foreign substances. Leukocytes are produced in the bone marrow. There are five main types of white blood cells, subdivided into two main groups: polymorphonuclear leukocytes (neutrophils, eosinophils, basophils) and mononuclear leukocytes (monocytes and lymphocytes). Moncytes that reside in tissue are called macrophages. When an infection is present, the production of leukocytes increases.

Leukotriene Antagonist/Leukotriene Formation Inhibitor: Drugs that block the effects of leukotrienes (leukotriene antagonists) or inhibit the formation of leukotrienes (leukotriene formation inhibitors). Leukotrienes are substances that are associated with an allergic response and inflammation. In the airways, they cause bronchial or alveolar narrowing and increase secretions. Drugs can interfere with leukotriene action by inhibiting their synthesis (for example, zileuton, ZYFLO®, Abbott Laboratories) or blocking the receptor to which they bind (for example, monteleukast, SINGULAIR®, Merck and Company, and others).

Lung Volume: The maximum volume the lungs can hold.

Mast Cell Stabilizer: A class of anti-inflammatory agents that work by preventing the release of substances in the body that cause inflammation. This is done by controlling the release of histamine from a white blood cells called mast cells. Examples include cromolyn and nedocromil.

Pharmaceutical agent or drug: A chemical compound or composition capable of inducing a desired therapeutic or prophylactic effect when properly administered to a subject. Pharmaceutical agents include, but are not limited to, anti-infective agents, anti-inflammatory agents, bronchodilators, enzymes, expectorants, leukotriene antagonists, leukotriene formation inhibitors, and mast cell stabilizers.

Pharmaceutically acceptable carriers: The pharmaceutically acceptable carriers useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of the suppressive ODNs herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Phosphatase Located on Chromosome 10 (PTEN): PTEN protein acts as a phosphatase to dephosphorylate phosphatidylinositol (3,4,5)-trisphosphate (PtdIns (3,4,5)$P_3$ or $PIP_3$). PTEN specifically catalyses the dephosporylation of the 3' phosphate of the inositol ring in $PIP_3$, resulting in the biphosphate product PIP$_2$ (PtdIns(4,5)P2). This dephosphorylation can result in inhibition of the AKT signaling pathway.

PTEN consists of a phosphatase domain and a C2 domain. The phosphatase domain contains the active site, which carries out the enzymatic function of the protein, while the C2 domain binds the phospholipid membrane. PTEN binds the membrane through its C2 domain, bringing the active site to the membrane-bound PIP$_3$ to dephosphorylate it. PTEN acts as part of a chemical pathway that signals cells to stop dividing and can cause cells to undergo apoptosis.

An exemplary amino acid sequence for human PTEN, and an exemplary mRNA sequence encoding this protein, can be found in GENBANK® Accession No. NM_000314.4 (Sep. 22, 2013), incorporated herein by reference. An Exemplary amino acid sequence for mouse PTEN, and an exemplary mRNA sequence encoding this protein, can be found in GENBANK® Accession No. NM_008960.2 (Sep. 22, 2013), incorporated herein by reference.

Protecting from a condition: Inhibiting or treating a condition such that the symptoms are significantly reduced or do not appear in a subject. "Inhibiting" a disease refers to inhibiting the full development of a condition, for example in a person who is at risk for inflammation of the lung and/or CIALI, such as from an exposure to a chemical agent. An example of a person at risk is someone who is exposed to a chemical agent, for example, one or more of chlorine, phosgene, sulfuric acid, ammonia, and acrolein. Inhibiting a disease process includes preventing the development of the disease. "Treatment" refers to a therapeutic intervention that ameliorates a sign or symptom of a disease or pathological condition, such as CALI, after it has begun to develop. Protection can be preventing CIALI or reducing CIALI form a subsequent exposure to the chemical insult, such as, but not limited to, resulting from exposure to one or more of chlorine, phosgene, sulfuric acid, ammonia, and acrolein.

Therapeutic agent: Used in a generic sense, it includes treating agents, prophylactic agents, and replacement agents.

Therapeutically effective amount: A quantity of a specified compound, such as a PTEN inhibitor, sufficient to achieve a desired effect in a subject being treated. For instance, this can be the amount sufficient to prevent advancement, or to cause regression of a disease, such as ALI, or which is capable of relieving or preventing signs or symptoms, such as pain, lung inflammation, fluid accumulation, or shortness of breath.

A therapeutically effective amount of an agent can be administered systemically or locally. In addition, an effective amount of an agent can be administered in a single dose, or in several doses, for example daily, during a course of treatment. However, the effective amount of the agent will be dependent on the preparation applied, the subject being treated, the severity and type of the affliction and/or exposure, and the manner of administration of the compound. For example, a therapeutically effective amount can vary from about 0.01 mg/kg body weight to about 1 g/kg body weight in some specific, non-limiting examples, or from about 0.01 mg/kg to about 60 mg/kg of body weight, based on efficacy.

The methods disclosed herein have equal applications in medical and veterinary settings. Therefore, the general term "subject" is understood to include all animals, including, but not limited to, humans.

Phosphatase Located on Chromosome 10 (PTEN) Inhibitor Compositions

It is disclosed herein that specific PTEN inhibitors can be used to treat acute lung injury, such as CIALI. Specific PTEN inhibitors of use are disclosed in PCT Publication No. 2005/097119, which is incorporated herein by reference. This PCT Publication discloses numerous PTEN inhibitors, of several general formulas (Compounds I-XIV), which can be used in the method disclosed herein, and discloses their synthesis.

The compound can also be selected from the following

| STRUCTURE | Compound Name | SF Number |
|---|---|---|
| | Deltamethrin; (S)-a-Cyano-3-phenoxybenzyl(1R)-cis-3-(2,2-dibromovinyl)-2,2-dimethylcyclopropanecarboxylate | SF1667-000 |
| | Alendronate, Sodium, Trihydrate | SF1669-100 |

-continued

| STRUCTURE | Compound Name | SF Number |
|---|---|---|
| | N-(9,10-Dioxo-9,10-dihydro-phenanthren-2-yl)-2,2-dimethyl-propionamide | SF1670-000 |
| | 5-Benzyl-3-furylmethyl (1R,S)-cis,trans-chrysanthemate | SF1671-000 |
| | Suramin, Sodium Salt; 8,8'-[carbonylbis]bis[imino-3,1-phenylenecarbonyl-imino(4-methyl-3,1-phenylene)carbonyl-imino]]bis-, hexasodium salt | SF1672-100 |
| | 4-Methoxyphenacyl Bromide | SF1673-000 |
| | 1,4-Dimethylendothall; 1,4-Dimethyl-7-oxabicyclo[2.2.1]heptane-2,3-dicarboxylic Acid | SF1676-000 |
| | Cantharidic Acid; 2,3-dimethyl-7-oxa-bicyclo[2.2.1]heptane-2,3-dicarboxylic acid | SF1679-000 |

-continued

| STRUCTURE | Compound Name | SF Number |
|---|---|---|
| | Sodium Stibogluconate; Antimony Sodium Gluconate | SF1680-000 |
| | 3,4-Dephostatin, Ethyl- | SF1681-000 |
| | Fenvalerate; a-Cyano-3-phenoxybenzyl-a-(4-chlorophenyl) isovalerate | SF1683-000 |
| | α-Naphthyl Acid Phosphate, Monosodium Salt | SF1684-100 |
| | β-Glycerophosphate Disodium Salt, Pentahydrate | SF1685-100 |
| | Endothall; 7-Oxabicyclo[2.2.1]heptane-2,3-dicarboxylic Acid | SF1686-000 |

| STRUCTURE | Compound Name | SF Number |
|---|---|---|
| | Cypermethrin; (R,S)-α-Cyano-3-phenoxybenzyl-3-(2,2-dichlorovinyl)-2,2-dimethylcyclopropanecarboxylate; (1R)-(R)-cyano(3-phenoxyphenyl) methyl 3-(2,2-dichlorovinyl)-2,2-dimethylcyclopropanecarboxylate | SF1687-000 | or a derivative or an acceptable salt thereof. See also PCT Publication No. WO 2005/097119, incorporated herein by reference.

"Pharmaceutically acceptable salts" includes salts of the active compounds which are prepared with relatively non-toxic acids or bases, depending on the particular substituents found on the compounds described herein. When the compounds contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, oxalic, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al. (1977) J. Pharm. Sci. 66:1-19). Some compounds contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound.

The PTEN inhibitor, such as, but not limited to, SF1670, can be formulated in a variety of ways. Pharmaceutical compositions are thus provided for both local (e.g. inhalational) use and for systemic use. Pharmaceutical compositions are used in the methods disclosed herein that include at least the PTEN inhibitor, such as, but not limited to, SF1670. The PTEN inhibitor can be formulated for use in human or veterinary medicine. While the PTEN inhibitor, such as, but not limited to, SF1670, will typically be used to treat human subjects, it can also be used to treat similar or identical diseases in veterinary subjects, such as non-human primates, dogs, cats, horses, and cows.

Pharmaceutical compositions that include at least a PTEN inhibitor, such as, but not limited to, SF1670, as an active ingredient, or that include both a PTEN inhibitor, such as, but not limited to, SF1670, and an additional respiratory agent as active ingredients, may be formulated with an appropriate solid or liquid carrier, depending upon the particular mode of administration chosen. Additional active ingredients include, for example, anti-infective agents, anti-inflammatory agents, bronchodilators, enzymes, expectorants, leukotriene antagonists, leukotriene formation inhibitors, and mast cell stabilizers. A suitable administration format may best be determined by a medical practitioner for each subject individually. Various pharmaceutically acceptable carriers and their formulation are described in standard formulation treatises, e.g., Remington's Pharmaceutical Sciences by E. W. Martin. See also Wang, Y. J. and Hanson, M. A., Journal of Parenteral Science and Technology, Technical Report No. 10, Supp. 42: 2S, 1988.

The dosage form of the pharmaceutical composition will be determined by the mode of administration chosen. For instance, in addition to injectable fluids, inhalational and oral formulations can be employed. Inhalational preparations can include aerosols, particulates, and the like. In general, the goal for particle size for inhalation is about 3 µm or less in order that the pharmaceutical reach the alveolar region of the lung for absorption. Oral formulations may be liquid (e.g., syrups, solutions, or suspensions), or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known, or will be apparent, to those of ordinary skill in the art.

The compositions or pharmaceutical compositions can be administered by any route, including parenteral administration, for example, intravenous, intramuscular, intraperitoneal, intrasternal, or intraarticular injection or infusion, or by sublingual, oral, topical, intranasal, or transmucosal administration, or by pulmonary inhalation. When PTEN inhibitors, such as, but not limited to, SF1670, are provided as parenteral compositions, e.g. for injection or infusion, they are generally suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate-acetic acid buffers. A form of repository or "depot" slow release preparation may be used so that therapeutically effective amounts of the preparation are delivered into the bloodstream over many hours or days following transdermal injection or delivery.

PTEN inhibitors, such as, but not limited to, SF1670, are also suitably administered by sustained-release systems. Suitable examples of sustained-release suppressive ODNs include suitable polymeric materials (such as, for example, semi-permeable polymer matrices in the form of shaped articles, e.g., films, or mirocapsules), suitable hydrophobic materials (such as, for example, an emulsion in an acceptable oil) or ion exchange resins, and sparingly soluble derivatives (such as, for example, a sparingly soluble salt). Sustained-release PTEN inhibitors, such as, but not limited to, SF1670, may be administered orally, rectally, parenterally, intracisternally, intravaginally, intraperitoneally, topically (as by powders, ointments, gels, drops or transdermal patch), bucally, or as an oral or nasal spray.

PTEN inhibitors can be suitably formulated to give controlled release. For example, the pharmaceutical compositions may be in the form of particles comprising a biodegradable polymer and/or a polysaccharide jellifying and/or bioadhesive polymer, an amphiphilic polymer, an agent modifying the interface properties of the particles and a pharmacologically active substance. These compositions exhibit certain biocompatibility features which allow a controlled release of the active substance. See U.S. Pat. No. 5,700,486.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring, and sweetening agents as appropriate.

For administration by inhalation, the PTEN inhibitor can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch.

Pharmaceutical compositions that include a PTEN inhibitor, such as, but not limited to, SF1670, as an active ingredient will normally be formulated with an appropriate solid or liquid carrier, depending upon the particular mode of administration chosen. The pharmaceutically acceptable carriers and excipients of use are conventional. For instance, parenteral formulations usually comprise injectable fluids that are pharmaceutically and physiologically acceptable fluid vehicles such as water, physiological saline, other balanced salt solutions, aqueous dextrose, glycerol or the like. Excipients that can be included are, for instance, proteins, such as human serum albumin or plasma preparations. If desired, the pharmaceutical composition to be administered may also contain minor amounts of non-toxic auxiliary substances, such as wetting or emulsifying agents, preservatives, and pH buffering agents and the like, for example sodium acetate or sorbitan monolaurate. Actual methods of preparing such dosage forms are known, or will be apparent, to those skilled in the art.

For example, for parenteral administration, PTEN inhibitors, such as, but not limited to, SF1670, can be formulated generally by mixing them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. A pharmaceutically acceptable carrier is a non-toxic solid, semisolid or liquid filler, diluent, encapsulating material or formulation auxiliary of any type.

Generally, the formulations are prepared by contacting the PTEN inhibitor, such as, but not limited to, SF1670, uniformly and intimately with liquid carriers or finely divided solid carriers or both. Then, if necessary, the product is shaped into the desired formulation. Optionally, the carrier is a parenteral carrier, and in some embodiments it is a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The pharmaceutical compositions that comprise a PTEN inhibitor, such as, but not limited to, SF1670, in some embodiments, can be formulated in unit dosage form, suitable for individual administration of precise dosages. The amount of active compound(s) administered will be dependent on the subject being treated, the severity of the affliction, and the manner of administration, and is best left to the judgment of the prescribing clinician. Within these bounds, the formulation to be administered will contain a quantity of the active component(s) in amounts effective to achieve the desired effect in the subject being treated.

The therapeutically effective amount of a PTEN inhibitor, such as, but not limited to, SF1670, will be dependent on the ODN utilized, the subject being treated, the severity and type of the affliction, and the manner of administration. For example, a therapeutically effective amount can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound (such as the PTEN inhibitor utilized), the age, weight, sex and physiological condition of the subject.

Therapeutically effective amounts of a PTEN inhibitor, such as, but not limited to, SF1670, for use in reducing lung injury, such as chemically induced acute lung injury, are those that reduce inflammation, induce epithelial wound repair, and/or improve breathing or oxygenation to a desired level. As will be recognized by those in the field, an effective amount of therapeutic agent will vary with many factors including the potency of the particular PTEN inhibitor, the age and weight of the patient, the patient's physical condition, the oxygenation level, and other factors.

Therapeutic Uses

A method is disclosed herein for treating or preventing acute lung injury in a subject, such as chemical induced acute lung injury (CIALI). In some embodiments, the method protects a subject from CIALI, such that symptoms of CIALI are significantly reduced and/or do not appear in a subject. In specific non-limiting examples, the subject does not have a pneumonia, such as a neutropenia-associated pneumonia. In other embodiments, the subject does not have a chronic lung condition such as chronic obstructive pulmonary disease (COPD) and/or reactive airway disease (such as asthma). The methods are of particular use to treat or protect a subject from exposure to agents used in chemical warfare.

In some embodiments, protection can be preventing CIALI or reducing CIALI form a subsequent exposure to the chemical insult. In other embodiments, protection can prevent or reduce symptoms of CIALI from a prior exposure to the chemical insult. In additional embodiments, the methods ameliorates a sign or symptom of CALI after it has begun to develop.

The method includes administering a therapeutically effective amount of the PTEN inhibitor, such as those disclosed in PCT Publication No. 2005/097119, incorporated herein by reference to a subject having or at risk of developing CIALI, thereby treating or inhibiting the CIALI in the subject. In specific non-limiting examples, the PTEN inhibitor is SF1670. The PTEN inhibitor can be administered locally, such as by inhalation. In another embodiment, the PTEN inhibitor, such as, but not limited to, SF1670, is administered systemically, such as by intravenous injection.

CIALI can be induced by any agent, including, but not limited to irritant gasses such as smoke, chlorine, phosgene, ammonia, sulfur mustard, chloramine, and/or methyl isocyante. The agent can be methyl isocyanate. In some embodiments, the subject has been exposed to, or is at risk for exposure to, chemical induced acute lung injury caused by chlorine, phosgene, sulfuric acid, ammonia, and/or acrolein gas. The subject can also be exposed to a water soluble gas (such as chlorine, ammonia, sulfur dioxide, or hydrogen chloride) or a less soluble gas (such as phosgene).

In some embodiments, the PTEN inhibitor can be administered to a subject at risk of exposure to a chemical that causes CIALI. Suitable subject include victims of a terrorist threat or catastrophic event such as but not limited, railroad car accidents or chemical plant disasters, military personnel, individuals that work in a chemical production facility, and individual exposed to, or at risk of exposure to, chemical warfare. In additional embodiments, the subject can be male or female. In further embodiments, subject can be an adult subject, a teenager, or a child. In certain embodiments, the subject is healthy. Ro example, the subject can be military or civilian personnel who are deployed to an area where there is a threat of exposure to irritant gasses. Alternatively, the healthy subject may be employed in a profession or place (such as a military base or chemical factory) where is a risk of exposure to irritant gasses. While in some embodiments the subject is human, use in veterinary subject is also contemplated.

In order to treat or prevent CIALI, a therapeutically effective amount of a PTEN inhibitor, such as, but not limited to, SF1670, (see above) is administered to the subject. Combinations of PTEN inhibitors, including SF1670, are also of use. Thus, in one embodiment, more than one PTEN inhibitors are administered to the subject. In several specific, non-limiting examples, at least two, at least three, or at least four PTEN inhibitors are administered to the subject.

In another embodiment an additional anti-infective agent, anti-inflammatory agent, bronchodilator, enzyme, expectorant, leukotriene antagonist, leukotriene formation inhibitor, anti-oxidant, or mast cell stabilizer is administered in conjunction with a PTEN inhibitor, such as, but not limited to, SF1670. The administration of the additional agent and the PTEN inhibitor can be sequential or simultaneous.

An effective amount of a PTEN inhibitor, such as, but not limited to, SF1670, can be administered in a single dose, or in multiple doses, for example hourly, during a course of treatment. In one embodiment, a therapeutically effective amount of a PTEN inhibitor, such as, but not limited to, SF1670, is administered as a single pulse dose, as a bolus dose, or as pulse doses administered over time, such as prior to a predicted exposure. Thus, in pulse doses, a bolus administration of a PTEN inhibitor, such as, but not limited to, SF1670, is provided, followed by a time period wherein no PTEN inhibitor is administered to the subject, followed by a second bolus administration. In specific, non-limiting examples, pulse doses of a PTEN inhibitor are administered during the course of a day, during the course of a week, or during the course of a month.

Local administration of the PTEN inhibitor, such as, but not limited to, SF1670, is performed by methods well known to those skilled in the art. By way of example, one method of administration to the lungs of an individual is by inhalation through the use of a nebulizer or inhaler. For example, the ODN can formulated in an aerosol or particulate and drawn into the lungs using a standard nebulizer well known to those skilled in the art. Suitable formulations are disclosed above. Alternatively the PTEN inhibitor may be provided as a mist in a closed environment in which the subject is located.

In other embodiments, the administration of the PTEN inhibitor, such as, but not limited to, SF1670, is systemic. Oral, intravenous, intraarterial, subcutaneous, intraperitoneal, intramuscular, and even rectal administration is contemplated. When administered by any route, a controlled release formulation can be utilized.

Administration may begin after exposure to the chemical agent or upon diagnosis of any form of acute lung injury. In some embodiments, administration begins prior to exposure to the chemical agent or other known causes of acute lung injury. In some embodiments, administration is at least 60 minutes prior to exposure to a chemical, such as 1, 2, 3, 4, 5, 6, 7, 8, 9, 10 hours prior to exposure to the chemical. In certain non-limiting examples, the PTEN inhibitor, such as SF1670, is administered about 5 to about 60 minutes prior to exposure to a chemical, such as about 45 minutes prior to exposure, such as to chlorine, phosgene, sulfuric acid, ammonia, and/or acrolein. In some embodiments the SF1670 is administered about 5 to about 60 minutes after exposure to a chemical that induces chemical induced acute lung injury, such as about 10 to about 50 minutes after exposure to the chemical, about 20 to about 40 minutes after exposure to the chemical, or about 25 to about 35 minutes after exposure to the chemical. For example, SF1670, can be administered about 30 minutes after exposure to the chemical.

In some embodiments, administration is immediate after exposure to a chemical, or hourly thereafter such as 1, 2, 3, 4, 5, 6, 7, 8, 9, 10 hours after chemical exposure. In some embodiments, administration may begin after chemical exposure but before symptoms develop to prevent delayed pulmonary edema or immediately after symptoms begin to develop.

The subject can receive additional therapies such as an analgesic, oxygen, humidification, and/or ventilator support. The subject can receive other anti-inflammatory therapy, such as a β2-agonist, dopamine, insulin, allopurinol, a corticosteroid, and/or a non-steroidal anti-inflammatory drugs (NSAIDs), such as ibuprofen.

Improvement can be detected in one or more symptoms of lung injury by one or more of spirometry, peak flow meter, detection of $CO_2$ levels in the blood, radiography, CT scanning, magnetic resonance imaging, bronchoscopy, or broncheolar lavage. The effectiveness of treatment can be measured by monitoring pulmonary function by methods known to those of skill in the art. For example, various measurable parameters of lung function can be studied before, during, or after treatment. Pulmonary function can be monitored by testing any of several physically measurable operations of a lung including, but not limited to, inspiratory flow rate, expiratory flow rate, and lung volume. A statistically significant increase, as determined by mathematical formulas well known to those skilled in the art, in one or more of these parameters indicates efficacy of the treatment.

The methods of measuring pulmonary function most commonly employed in clinical practice involve timed measurement of inspiratory and expiratory maneuvers to measure specific parameters. For example, FVC measures the total volume in liters exhaled by a patient forcefully from a deep initial inspiration. This parameter, when evaluated in conjunction with the FEV1, allows bronchoconstriction to be quantitatively evaluated. A statistically significant increase, as determined by mathematical formulas well known to those skilled in the art, in FVC or FEV1 reflects a decrease in bronchoconstriction, and indicates that treatment is effective.

A problem with forced vital capacity determination is that the forced vital capacity maneuver (i.e., forced exhalation from maximum inspiration to maximum expiration) is largely technique dependent. In other words, a given subject may produce different FVC values during a sequence of consecutive FVC maneuvers. The FEF 25-75 or forced expiratory flow determined over the midportion of a forced exhalation maneuver tends to be less technique dependent than the FVC. Similarly, the FEV1 tends to be less technique-dependent than FVC. Thus, a statistically significant increase, as determined by mathematical formulas well known to those skilled in the art, in the FEF 25-75 or FEV1 reflects a decrease in bronchoconstriction, and indicates that the therapy is effective.

In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest airflow rate in liters per minute during a forced maximal exhalation, is well correlated with overall pulmonary function in a patient with asthma and other respiratory diseases. Thus, a statistically significant increase, as determined by mathematical formulas well known to those skilled in the art, in the peak expiratory flow following administration of a PTEN inhibitor, such as, but not limited to, SF1670, indicates that the therapy is effective.

The effectiveness of treatment can be measured by time a subject requires intensive care, as in some embodiments, days in the intensive care unit. The effectiveness of treatment can be measured as enhanced survival, as in some embodiments, extension of days alive or percentage of subjects alive at 14 or 30 days. In some embodiments, the methods reduce the time that mechanical ventilation is required following exposure to a chemical.

The following examples are provided to illustrate particular features of certain embodiments, but the scope of the claims should not be limited to those features exemplified.

EXAMPLES

Figure 1:
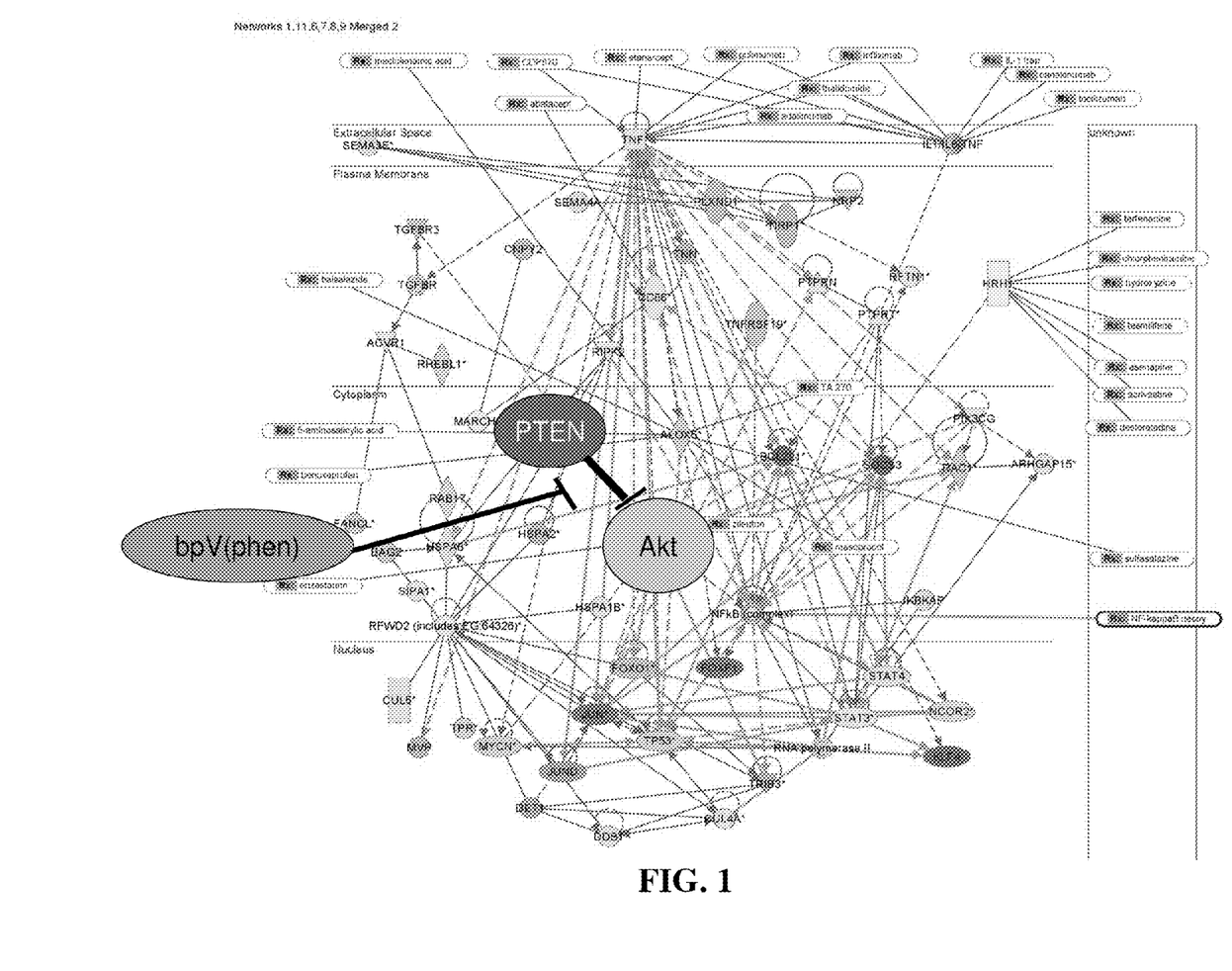
FIG. 1. Interactome of the genes identify by haplotype association mapping of 40 mice strains following chemical-induced acute lung injury. A major hub was Akt1 (protein kinase B), a protein associated with increased survival in cancer cells. The endogenous inhibitor PTEN is an inhibitor of Akt1. This provided a target of PTEN inhibition by bpV(phen), which could be permissive for added Akt activation and increased survival during acute lung.

Mouse models of five common pulmonary irritant agents (acrolein, ammonia, chlorine, phosgene, and sulfuric acid) were characterized, and the v-AKT1 thymoma viral oncogene homolog 1 (AKT1) was implicated in chemical-induced acute lung injury (CALI). When activated, AKT1 phosphorylates and inhibits components of the cell death machinery (see FIG. 1). It was determined that inhibition of phosphatase and tensin homolog deleted on chromosome 10 (PTEN), a phosphatase that limits AKT1 activity, protects against CIALI in vivo. SF1670 was effective at treating CIALI in an animal model system.

Example 1

Objective:

To demonstrate efficacy of PTEN inhibitor potassium bisperoxo (1,10-phenanthroline)oxovanadate [bpV(Phen)] with or without antioxidant therapy in reducing mortality after 450 ppm chlorine inhalation for 45 minutes.

Criteria for Success:

Reduced mortality by ≥20% when bpV(Phen) alone is administered 30 min after chlorine challenge as compared to chlorine alone in mice. Further reduced mortality by bpV(Phen) plus antioxidants administered 30 min after chlorine challenge as compared to antioxidants alone is administered 30 min after chlorine challenge in mice. An additional group of mice exposed to filtered air.

Results:

It was determined that a dose of 300 ppm chlorine for 45 minutes was sufficient to kill the mice In initial studies, mice were exposed to chlorine and 0.7 μmol bpV(Phen) was administered 30 minutes post exposure and survival monitored hourly for 48 hours and every 4 hours thereafter. Administration was by intra-peritoneal route. The survival curves were not different from saline injected control. For these studies, the dose used was 0.7 μmol. However, this dose may not have been effective (see below).

Figure 2:
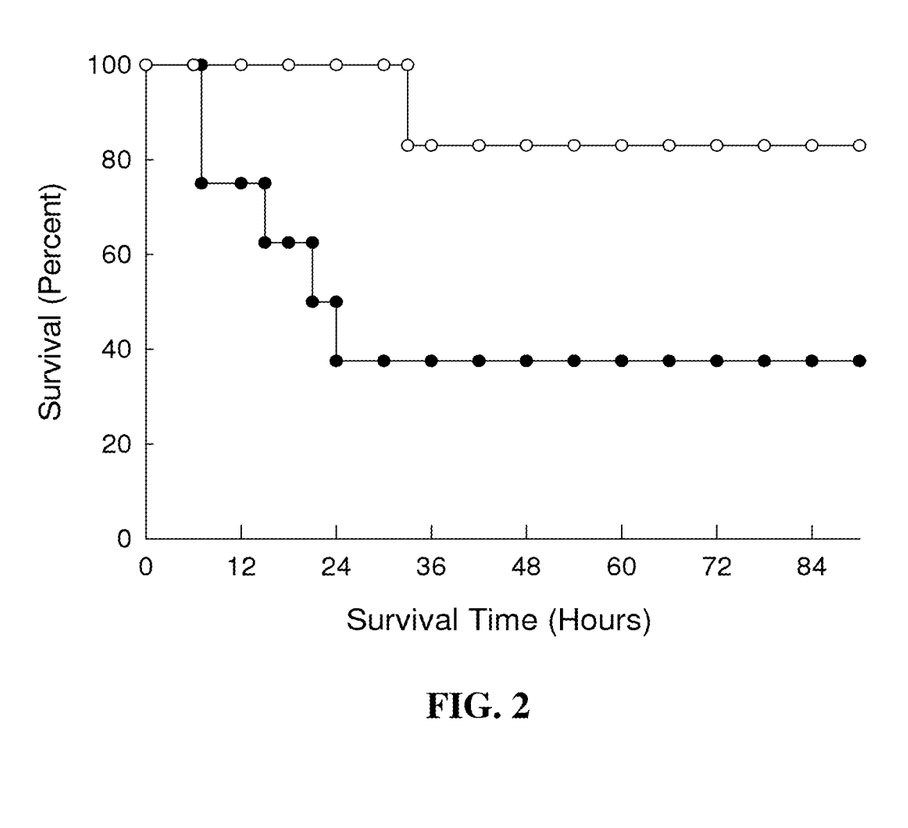
FIG. 2. SF1670 [N(9,10-dioxo-9,10-di-hydrophenanthren-2-yl) pivalamide] enhances survival in mice during chlorine-induced acute lung injury. Mice were exposed to 300 ppm chlorine for 45 min and then injected with 5 mg/kg SF1670 intraperiotoneally (i.p.) 30 minutes (min) post exposure. Survival was monitored hourly for 48 hours (h) and every 4 h thereafter. SF1670 (5 mg/kg) by intra-peritoneal administration provided 83% survival (open circles) as compared to 37.5% with saline treatment (solid circles) in the mice exposed to 300 chlorine for 45 min ppm.

Results:

In this animal model, SF1670 pretreatment enhanced survival in mice challenged with pneumonia following E. coli infection. SF1670 also inhibits PTEN ($IC_{50}$=2 μM) but it does not contain potassium or vanadium, which may produce nonspecific phosphatase inhibitory effects. SF1670 (5 mg/kg) by intra-peritoneal administration provided 83% survival as compared to 37.5% with saline treatment in the mice exposed to 300 chlorine for 45 min ppm (FIG. 2). This is a net improvement of 45.5% in survival.

Example 2

Objective:

Demonstrate efficacy by intra-peritoneal administration of PTEN inhibitor potassium bisperoxo(1,10-phenanthroline) oxovanadate [bpV(Phen)] with or without antioxidant therapy in reducing mortality after 5 ppm phosgene inhalation for 45 minutes.

Criteria for Success:

Reduced mortality by ≥20% when bpV(Phen) alone is administered 30 min after phosgene challenge as compared to phosgene alone in mice. Further reduced mortality by bpV(Phen) plus antioxidants administered 30 min after phosgene challenge as compared to antioxidants alone is administered 30 min after phosgene challenge in mice. An additional group of mice was exposed to filtered air.

Results:

The dose of 5 ppm phosgene for 45 minutes was insufficient to kill the mice. The dose was increased to 30 ppm phosgene for 1 hour. In initial studies, mice were exposed to phosgene and 0.7 μmol bpV(Phen) was administered 30 min post exposure and survival monitored hourly for 48 h and every 4 h thereafter. The survival curves were not different from saline injected control.

Figure 3:
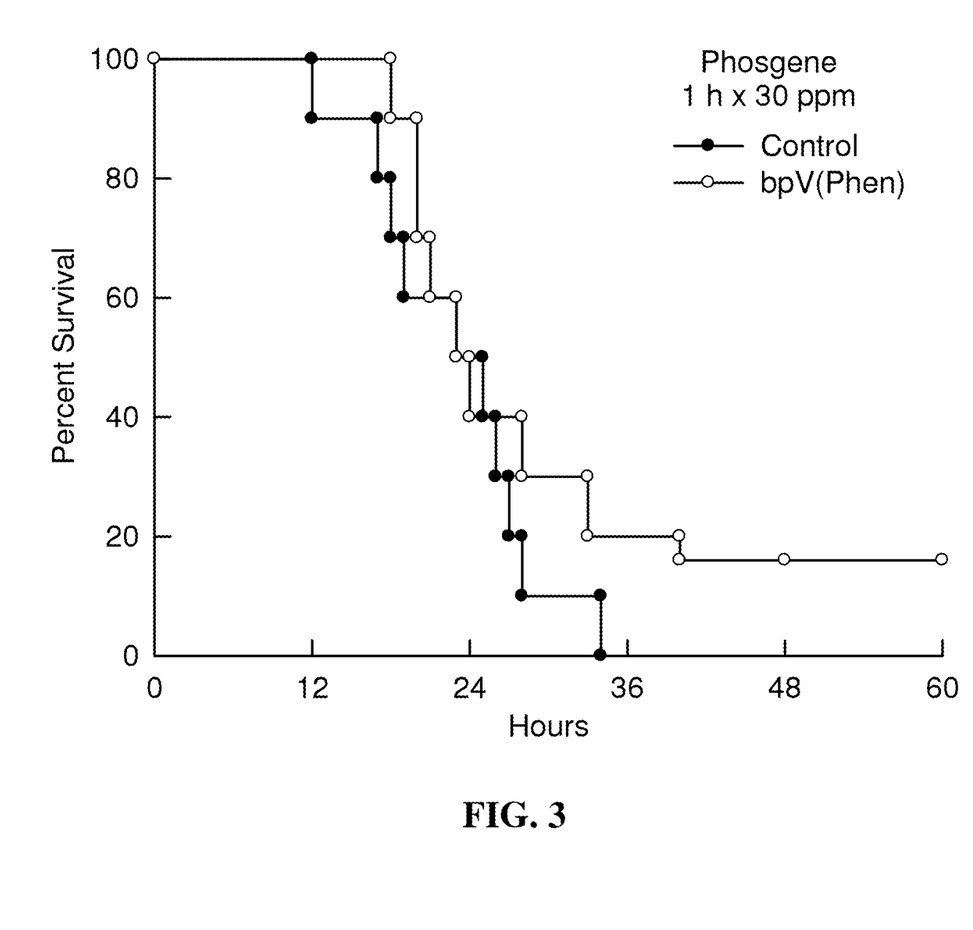
FIG. 3. Potassium bisperoxo(1,10-phenan-throline)oxovanadate [bpV(Phen)] enhances survival in mice during phosgene-induced acute lung injury. Mice were exposed to 30 ppm phosgene and then injected with 0.3 μmol bpV (Phen) i.p. 30 min post exposure. Survival was monitored hourly for 48 h and every 4 h thereafter.

In previous studies with oleic acid-induced lung injury, it was reported (Lai J P et al. Br J Pharmaol 156:189, 2009) that there was a biphasic dose response effect of bpV(Phen) over a dosage range studied (0.05-1.6 μmol). The most significant reduction in BALF protein content was observed between 0.1 and 0.4 μmol, whereas at the lower (0.05 μmol) and higher (0.8 and 1.6 μmol) doses the benefit was diminished. BpV(phen) treatment alone over the same dose range showed no evidence of lung injury. Based on that study, it was determined that the dose should be 0.7 μmol. However, this dose may have been too high. The dose was thus decreased to 0.3 μmol. While this dose did improve survival (FIG. 3), there were two shortcomings with this compound. Specifically, it had is a very narrow effective dose range (less than 1 log). Without being bound by theory, the narrow dose range may be related to the mode of action of this compound. BpV(phen) is a phosphatase inhibitor and the higher doses could inhibit beneficial pathways that used de-phosphorylation to inactive enzymes. In addition, it is a potassium salt. Second, while this compound was beneficial in oleic acid-induced acute lung injury, it was only somewhat beneficial for chlorine and for phosgene, as disclosed herein. Furthermore, it was not effective at the higher doses in acrolein. Moreover, the compound did not reduce mortality by >20% in phosgene, which was the target for this milestone (FIG. 3).

Figure 4:
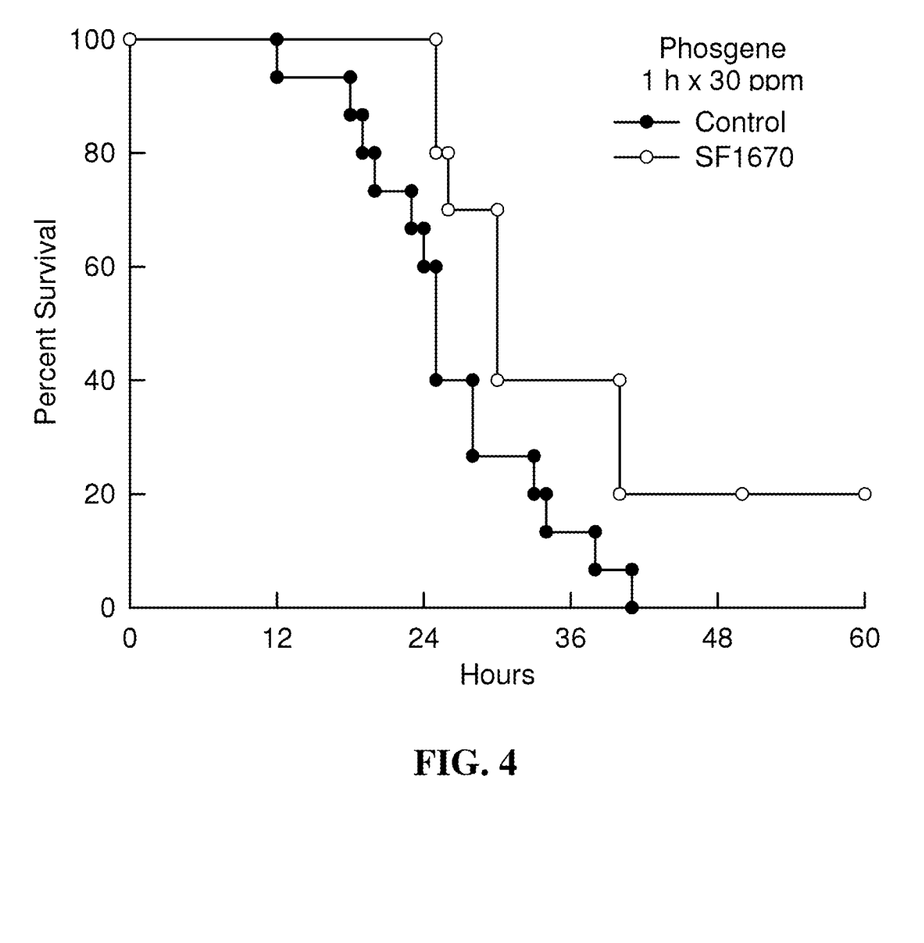
FIG. 4. SF1670 [N(9,10-dioxo-9,10-di-hydrophenanthren-2-yl) pivalamide] enhances survival in mice during phosgene-induced acute lung injury. Mice were exposed to 30 ppm phosgene and then injected with 5 mg/kg SF1670 i.p. 30 min post exposure. Survival was monitored hourly for 48 h and every 4 h thereafter.

SF1670 (5 mg/kg) by intra-peritoneal administration provided 20% survival in the mice exposed to 30 ppm phosgene for 1 hour (FIG. 4). Thus, SF1670 was more effective than bpV(Phen) in these studies.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A method of protecting a subject from chemical induced acute lung injury, comprising administering to a subject exposed to a chemical, wherein the chemical is acrolein, chlorine or phosgene, a therapeutically effective amount of N(9,10-dioxo-9,10-di-hydrophenanthren-2-yl) pivalamide (SF1670), thereby protecting the subject from the chemical induced acute lung injury.

2. The method of claim 1, wherein the chemical is chlorine.

3. The method of claim 1, wherein the subject is human.

4. The method of claim 1, wherein protecting the subject from chemical induced acute lung injury comprises reducing a symptom of the chemical induced acute lung injury.

5. The method of claim 1, wherein the N(9,10-dioxo-9,10-di-hydrophenanthren-2-yl) pivalamide (SF1670) is administered about 5 to about 60 minutes following exposure to the chemical that induces chemical induced acute lung injury.

6. The method of claim 5, wherein the N(9,10-dioxo-9,10-di-hydrophenanthren-2-yl) pivalamide (SF1670) is administered about 30 minutes following exposure to the chemical.

7. The method of claim 1, wherein the chemical is phosgene.

8. The method of claim 1, comprising detecting an improvement in one or more symptoms of lung injury by one or more of spirometry, peak flow meter, detection of $O_2$ and/or $CO_2$ levels in the blood, radiography, CT scanning, magnetic resonance imaging, bronchoscopy, or broncheoalveolar lavage.

9. The method of claim 1, wherein the N(9,10-dioxo-9,10-di-hydrophenanthren-2-yl) pivalamide (SF1670) is administered systemically.

10. The method of claim 1, wherein the N(9,10-dioxo-9,10-di-hydrophenanthren-2-yl) pivalamide (SF1670) is administered by inhalation.

11. The method of claim 1, wherein the N(9,10-dioxo-9,10-di-hydrophenanthren-2-yl) pivalamide (SF1670) promotes epithelial wound repair.

12. The method of claim 1, wherein the subject is a healthy subject.

13. The method of claim 1, further comprising administering to the subject an effective amount of an anti-inflammatory agent, a bronchodilator, an expectorant, a leukotriene antagonist, a leukotriene formation inhibitor, an anti-oxidant, or a mast cell stabilizer.

14. The method of claim 1, further comprising administering to the subject a therapeutically effective amount of an antioxidant.

15. The method of claim 1, wherein the chemical is acrolein.

* * * * *